United States Patent
Tseng

[19]

[11] Patent Number: 5,936,414
[45] Date of Patent: Aug. 10, 1999

[54] BRAKE OIL DETECTOR

[76] Inventor: Tien-Tsai Tseng, No. 771, Lin-Sen Road, Wu-Feng, Taichung Hsien, Taiwan

[21] Appl. No.: 08/934,651

[22] Filed: Sep. 22, 1997

[51] Int. Cl.[6] .................................................. G01N 27/02
[52] U.S. Cl. ........................... 324/696; 324/698; 73/53.05
[58] Field of Search ............................. 73/53.01, 53.05, 73/61.41, 61.43; 324/663, 664, 693, 694, 696, 698, 439, 446

[56] References Cited

U.S. PATENT DOCUMENTS 4,052,667 10/1977 Schwartz .................. 324/439
5,644,239 7/1997 Huang et al. ............. 324/439

Primary Examiner—Michael Brock
Attorney, Agent, or Firm—Rosenberg, Klein & Bilker

[57] ABSTRACT

A brake oil detector is disclosed. It includes a housing formed with a through hole on one side, a circuit board disposed in the housing and having a wire extending through the through hole to outer side of the housing, a pivotable rotary shaft disposed in the through hole and an extension arm disposed at one end of the rotary shaft and having a free end disposed with a sensor connected to the circuit board by the wire. The sensor of the extension arm is extended into a brake oil tank to check out the viscosity of the brake oil and judge whether it is necessary to replace the brake oil.

7 Claims, 5 Drawing Sheets

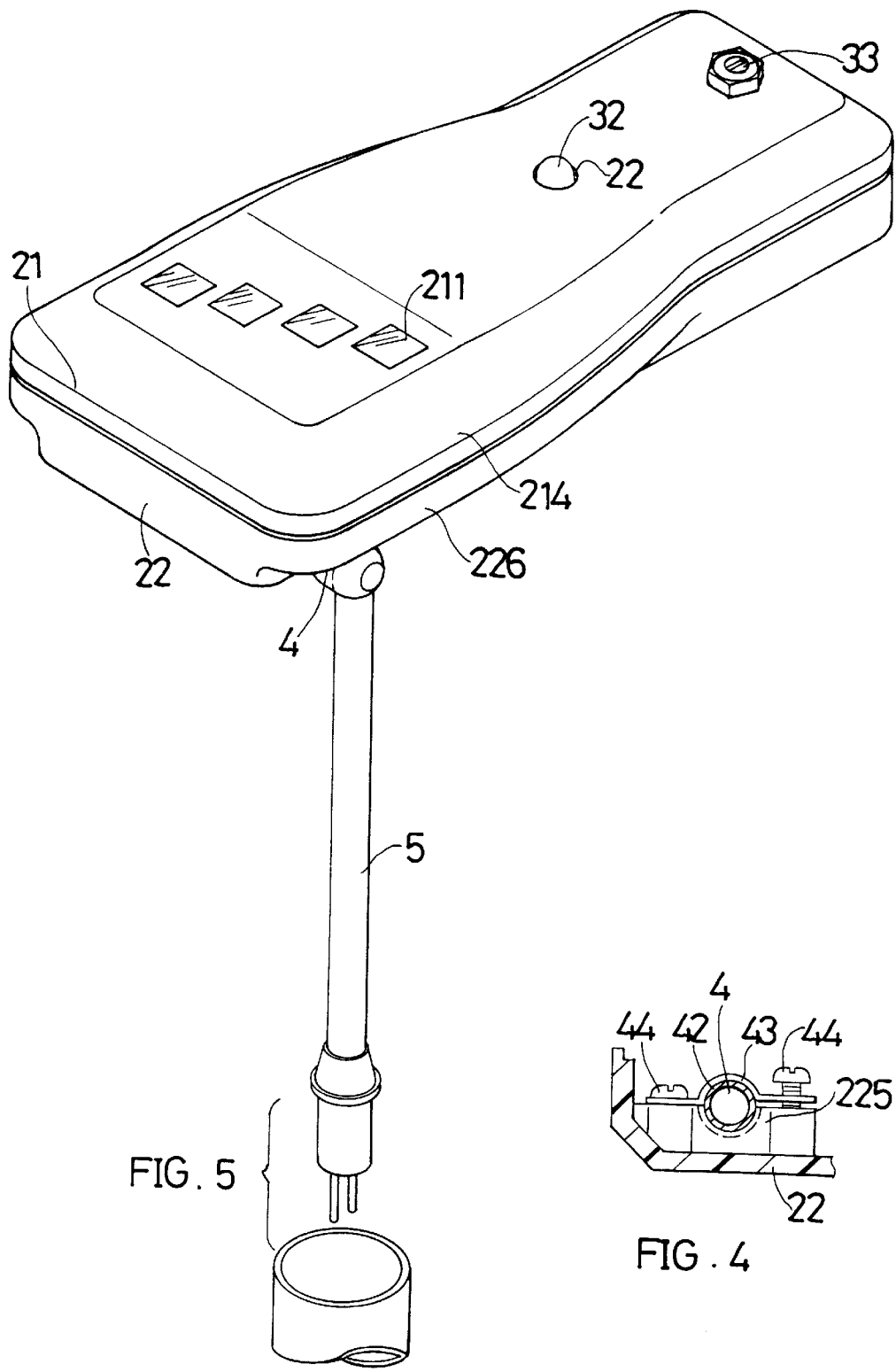

BRAKE OIL DETECTOR

BACKGROUND OF THE INVENTION

The present invention relates to a brake oil detector in which an extension arm is pivotally disposed on one side of a housing and disposed with a sensor at free end. The sensor is connected to a circuit board in the housing by a wire.

FIG. 1 shows an existing brake oil detector including a main body 1 disposed with a circuit board (not shown) and a flexible arm 11 extending from one side of the main body 1. The free end of the flexible arm 11 has a detector 12 connected to the circuit board by a wire (not shown), whereby the detection signal can be transmitted to a processor on the circuit board. A detection button 13 and an adjustment switch 14 are disposed on the main body 1 to obtain the detection signal. A signal lamp 15 is disposed on the main body 1 for indicating the detection result.

According to the above arrangement, in use, a user must hold the main body 1 with one hand and take the flexible arm 11 with the other hand to insert the flexible arm 11 into a brake oil tank (not shown). Then the other hand lets go the flexible arm 11 to depress the detection button 13 and the adjustment switch 14 to perform the detection operation. Such procedure is quite inconvenient. After the detection is completed, the user needs to take out the flexible arm 11 with one hand and wipe off the brake oil attached to the detector 12. Moreover, it is difficult to store the extending flexible arm 11 which is subject to damage.

SUMMARY OF THE INVENTION

It is therefore a primary object of the present invention to provide a brake oil detector in which an extension arm is pivotally disposed on one side of a housing and disposed with a sensor at free end. In use, the extension arm is rotated outward and directly inserted into a brake oil tank. After used, the extension arm is rotated back to its home position and hidden under a projection of the housing. The detection can be easily and quickly performed and the extension arm can be stored without being damaged.

The present invention can be best understood through the following description and accompanying drawings, wherein:

BRIEF DESCRIPTION OF THE DRAWINGS

FIG. 4 is a sectional view showing the relationship between the rotary shaft and the lower casing of the first embodiment;

FIG. 5 shows the operation of the first embodiment of the present invention.

DETAILED DESCRIPTION OF THE PREFERRED EMBODIMENTS

Figure 1:
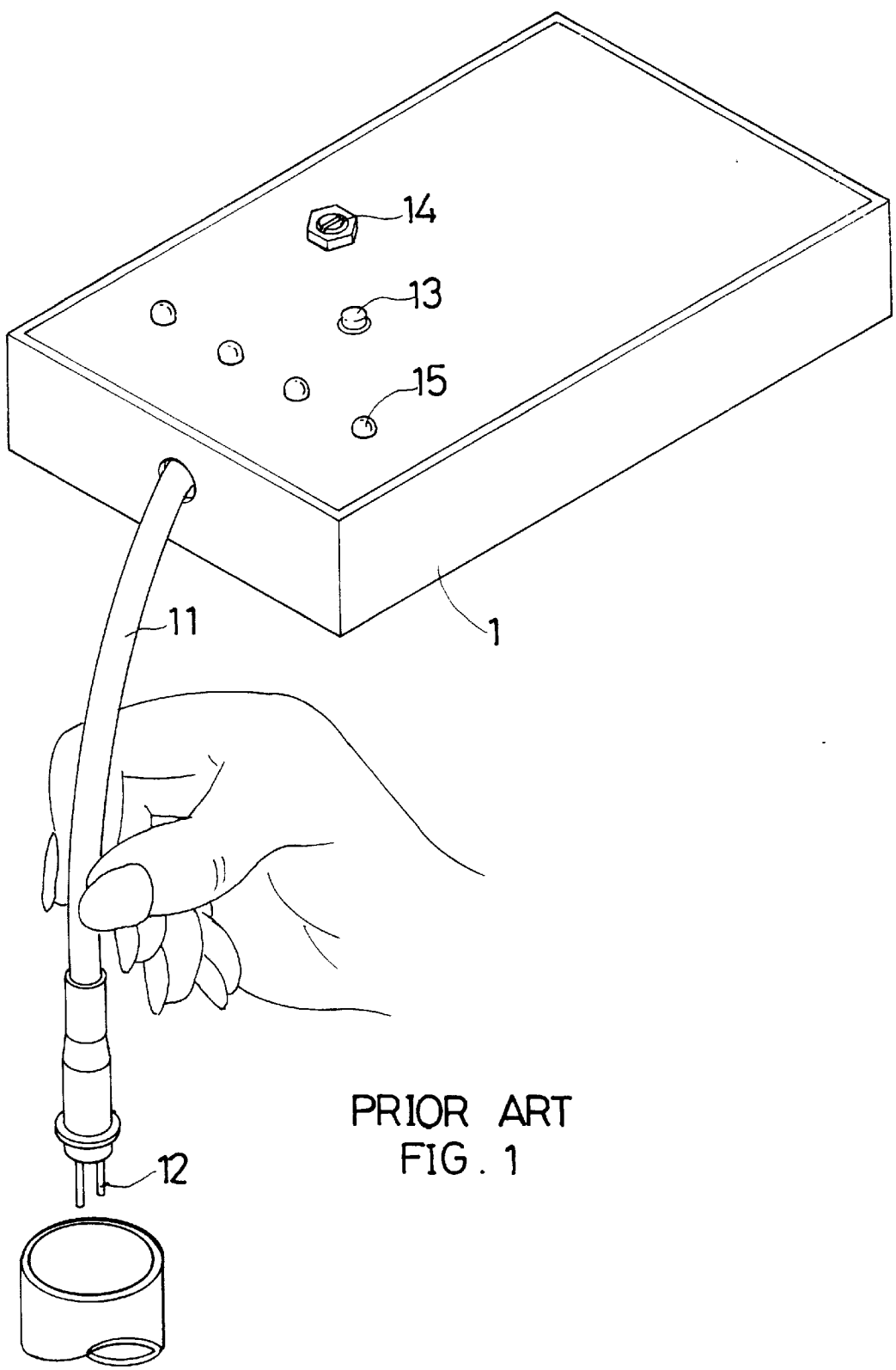
FIG. 1 is a perspective view of a conventional brake oil detector.
Figure 2:
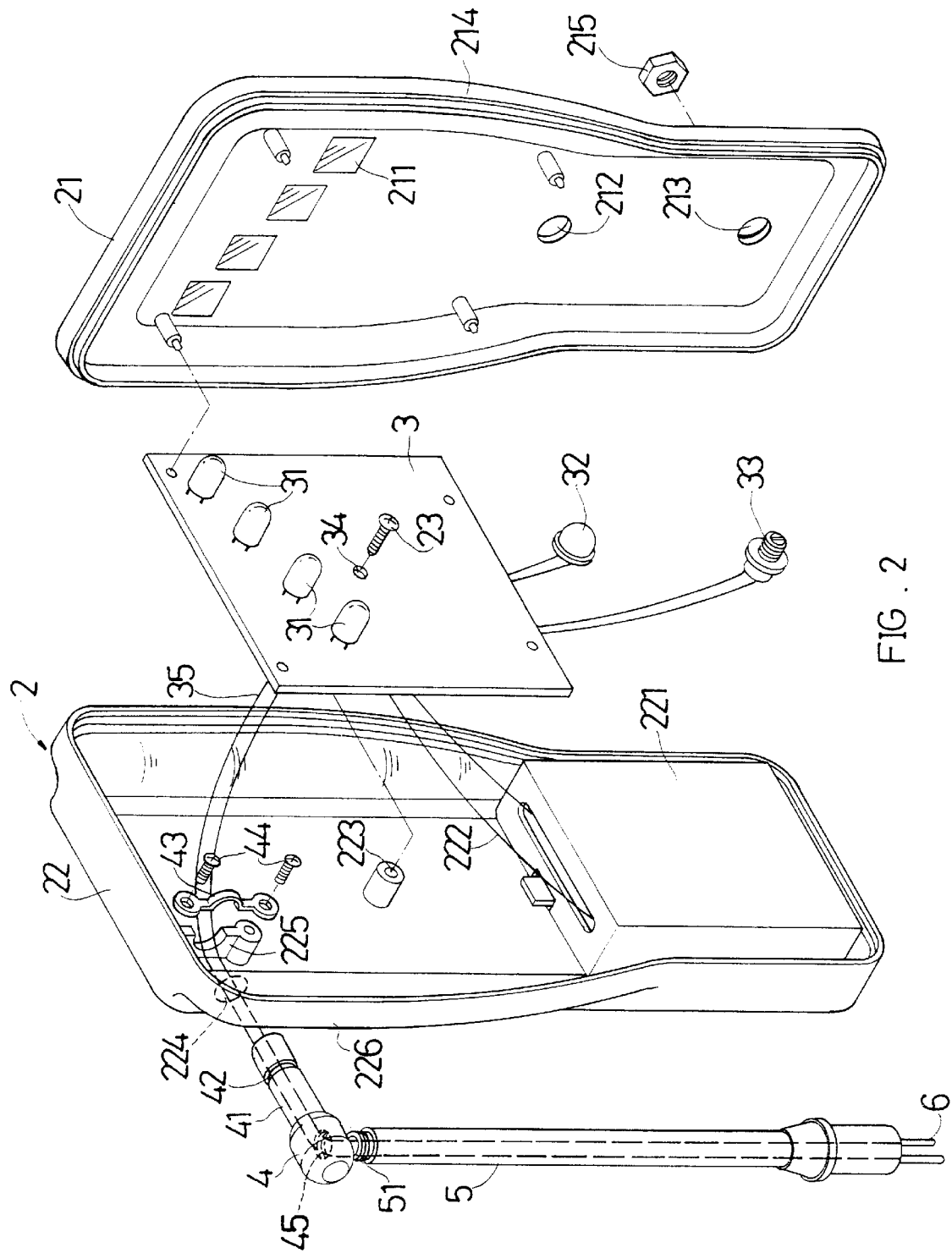
FIG. 2 is a perspective exploded view of a first embodiment of the present invention.
Figure 3:
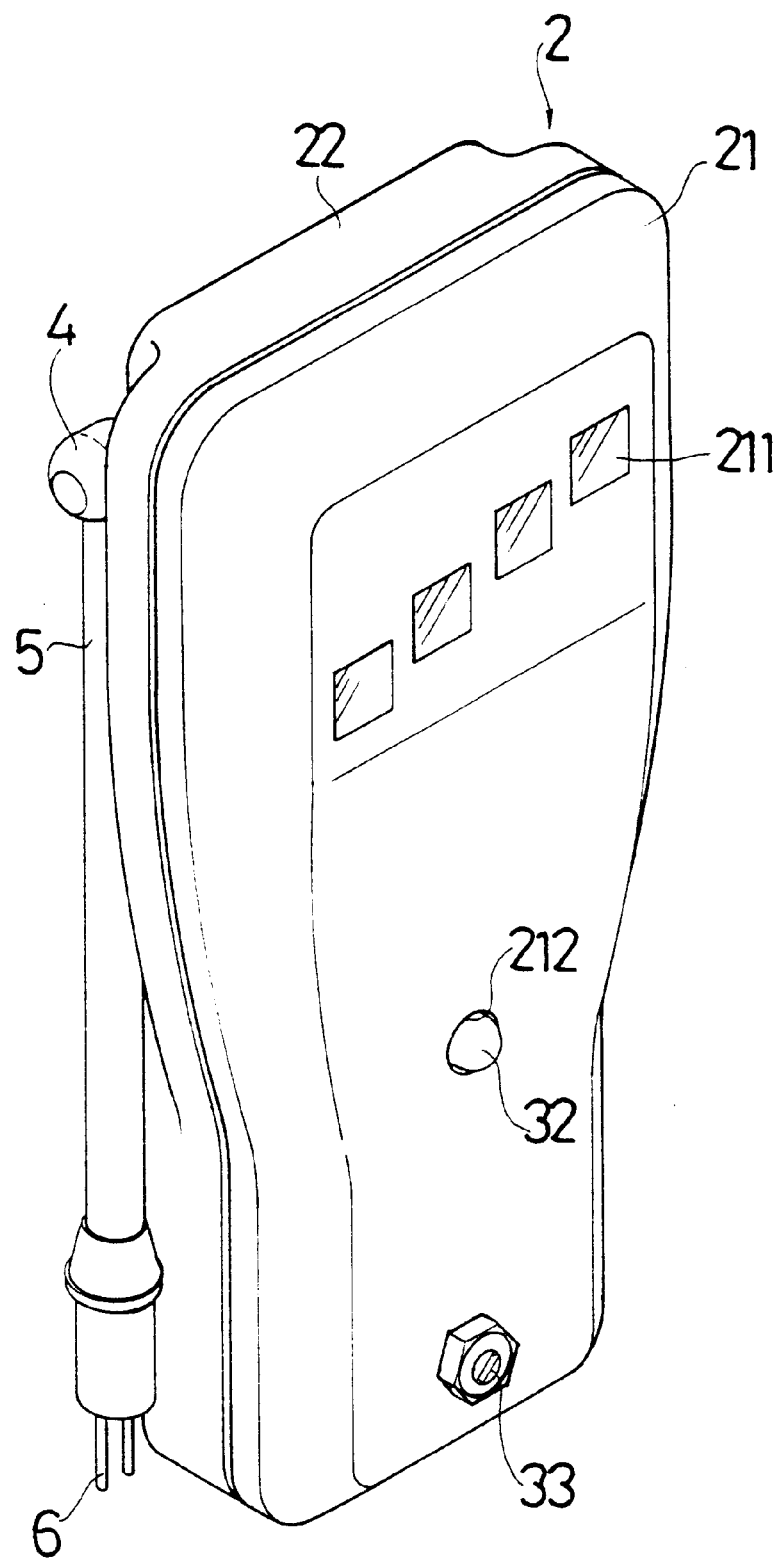
FIG. 3 is a perspective assembled view of the first embodiment of FIG. 2.

Please refer to FIGS. 2 and 3. The brake oil detector of the present invention includes a housing 2, a circuit board 3, a rotary shaft 4, an extension arm 5 and a sensor 6.

The housing 2 is composed of an upper and a lower casings 21, 22 mating with each other. The upper casing 21 is formed with multiple signal light shades 211 for multiple LEDs 31 (LED means Light-Emitting Diode) arranged on the circuit board 3, a control hole 212 through which a detection button 32 of the circuit board 3 extends out, and an adjustment hole 213 through which an adjustment button 33 of the circuit board 3 extends out. The upper casing 21 is tightened by a nut 215. The lower casing 22 is formed with a cell chamber 221 connected to the circuit board 3 by an extending wire 222. A screw 23 is passed through a locating hole 34 of the circuit board 3 to be screwed into a thread hole 223 of the lower casing 22. A through hole 224 is formed on one side of the lower casing 22 for communicating inner side with outer side of the housing 2. A locating wall 225 is disposed beside the through hole 224. The lateral edges of the lower casing 22 and upper casing 21 on the same side as the through hole 224 are formed with projections 226, 214.

The circuit board 3 is disposed in the housing 2 and a wire 35 extends from the circuit board 3 out of the through hole 224.

The rotary shaft 4 is disposed in the through hole 224 and has a locating section 41 extending into the housing 2. The locating section 41 is formed with an annular groove 42 engaged with the locating wall 225 of the lower casing 22 to prevent the locating section 41 from axially moving. A locating plate 43 is disposed on upper side of the locating section 41. Referring to FIG. 4, the locating plate 43 is secured on the locating wall 225 by a screw 44 to press the locating section 41, whereby when rotated, the rotary shaft 4 suffers a certain resistance. The wire 35 of the circuit board 3 is conducted through the rotary shaft 4.

The extension arm 5 is formed with outer thread 51 screwed into a thread hole 45 of the rotary shaft 4. A free end of the extension arm 5 is disposed with a sensor 6 connected with the wire 35.

The extension arm 5 is pivotally disposed on the housing 2 via the rotary shaft 4 and stopped by the projections 226, 214 of the housing 2, whereby the extension arm 5 can be stored without being damaged. In use, the extension arm 5 is pivoted outward and inserted into the brake oil tank (not shown). Then the detection button 32 is pressed down to check out whether it is necessary to replace the brake oil. Therefore, the present invention can be operated easily and quickly.

The extension arm can be inserted into a recess of the rotary shaft and fixedly adhered thereto by ultrasonic wave.

Figure 6:
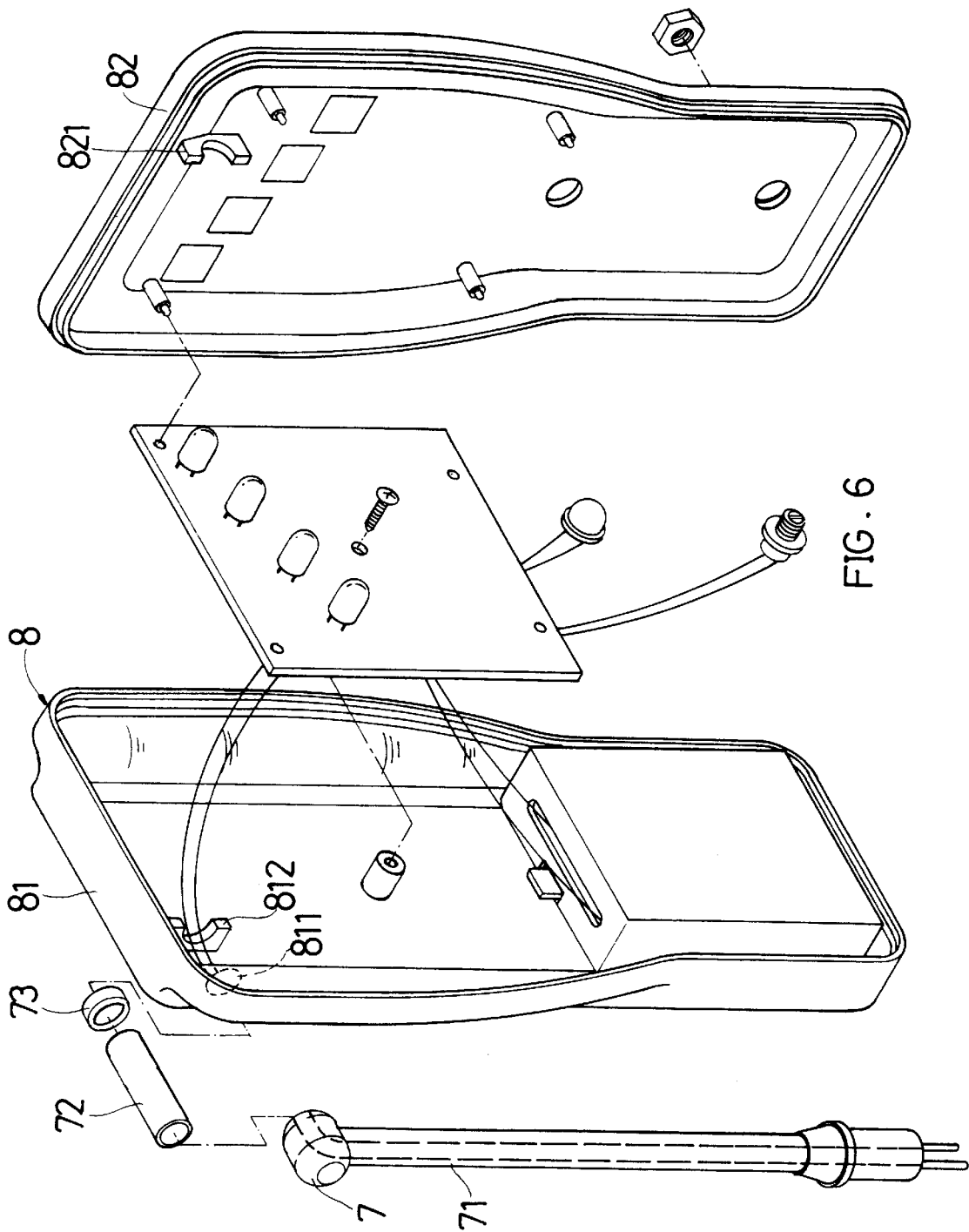
FIG. 6 is a perspective exploded view of a second embodiment of the present invention.

FIG. 6 shows a second embodiment of the present invention, which is different from the first embodiment in that the rotary shaft 7 and the extension arm 71 are integrally formed, while the rotary shaft 7 is assembled with the locating section 72 as two elements. A pad member 73 is fitted around the locating section 72 and inserted into the through hole 811 of the lower casing 81 of the housing 8. A locating wall 812 of the lower casing 81 and a locating wall 821 of the upper casing 82 respectively radially abut against the locating section 72 from upper and lower sides, whereby by means of the frictional force between the pad member 73 and the locating walls 812, 821, the extension arm 71 will also suffer a certain resistance when rotated.

It is to be understood that the above description and drawings are only used for illustrating some embodiments of the present invention, not intended to limit the scope thereof. Any variation and derivation from the above description and drawings should be included in the scope of the present invention.

What is claimed is:

1. A brake oil detector comprising a housing formed with a through hole on one side, a circuit board disposed in the housing and having a wire extending through the through hole to outer side of the housing, a pivotable rotary shaft disposed in the through hole and an extension arm disposed at one end of the rotary shaft and having a free end disposed with a sensor connected to the circuit board by the wire.

2. A brake oil detector as claimed in claim 1, wherein the housing is composed of an upper and a lower casings mating with each other, the upper casing being formed with multiple signal light shades for multiple LEDs arranged on the circuit board, a control hole through which a detection button of the circuit board extends out, and an adjustment hole through which an adjustment button of the circuit board extends out, the lower casing being formed with a cell chamber connected to the circuit board by an extending wire, a screw being passed through a locating hole of the circuit board to be screwed into a thread hole of the lower casing.

3. A brake oil detector as claimed in claim 2, wherein the rotary shaft is disposed in the through hole of the lower casing and has a locating section extending into the housing, the locating section being formed with an annular groove engaged with a locating wall of the lower casing to prevent the locating section from axially moving, a locating plate being disposed on upper side of the locating section, the locating plate being secured on the locating wall to press the locating section, whereby when rotated, the rotary shaft suffers a certain resistance.

4. A brake oil detector as claimed in claim 1, wherein a lateral edge of the housing on the same side as the through hole is disposed with a projection for stopping the extension arm from being upward pivoted.

5. A brake oil detector as claimed in claim 1, wherein the extension arm is formed with outer thread screwed into a thread hole of the rotary shaft.

6. A brake oil detector as claimed in claim 1, wherein the extension arm can be inserted into a recess of the rotary shaft and fixedly adhered thereto by ultrasonic wave.

7. A brake oil detector as claimed in claim 1, wherein the rotary shaft and the extension arm are integrally formed and the rotary shaft is assembled with a locating section, a pad member being fitted around the locating section and inserted into the through hole of the housing, a locating wall of the housing radially abutting against the locating section to exert a frictional force onto the pad member when rotating the extension arm.

\* \* \* \* \*